United States Patent [19]

Lewis et al.

[11] 4,202,984
[45] May 13, 1980

[54] β-(HEXAHYDRO-2,6-METHANO-3-BENZAZOCIN-11-YL)PROPIONIC ACIDS, ESTERS AND AMIDES

[75] Inventors: Thomas R. Lewis, Bethlehem; William F. Michne, Poestenkill, both of N.Y.

[73] Assignee: Sterling Drug Inc., New York, N.Y.

[21] Appl. No.: 35,937

[22] Filed: May 4, 1979

Related U.S. Application Data

[63] Continuation-in-part of Ser. No. 886,650, Mar. 15, 1978, abandoned.

[51] Int. Cl.² .................................................. C07D 221/26
[52] U.S. Cl. ...................................... 546/97; 424/267; 546/43; 546/74
[58] Field of Search ............................. 546/97, 74

[56] References Cited

U.S. PATENT DOCUMENTS

| | | |
|---|---|---|
| 3,250,678 | 5/1966 | Archer .................................. 424/267 |
| 3,733,330 | 5/1973 | Schubert et al. ........................ 546/97 |
| 3,776,914 | 12/1973 | Atsumi ................................. 546/97 |
| 3,932,422 | 1/1976 | Michne ................................ 546/97 |

*Primary Examiner*—Alan L. Rotman
*Assistant Examiner*—Richard A. Schwartz
*Attorney, Agent, or Firm*—William G. Webb; B. Woodrow Wyatt

[57] ABSTRACT

β-[3-$R_1$-6(eq)-$R_4$-7-$R_2''$-8-$R_2$-9-$R_2'$-10-$R_2'''$-11(ax)-$R_3$-1,2,3,4,5,6,-hexahydro-2,6-methano-3-benzazocin-11(eq)-yl]propionic acids, esters and amides, useful as analgesics and narcotic antagonists, are prepared by heating, with formic acid in an organic solvent or with certain ammonium formates, certain di-lower-alkyl 1-$R_1$-4aα-$R_3$-5α-$R_4$-6-$R_2''$-7-$R_2$-8-$R_2'$-9-$R_2'''$-1,2,3,4,4a,5,10,10a-octahydro-2,5-methanobenzo[g]quinoline-3,3-dicarboxylates, to prepare the esters, hydrolysis of the latter to prepare the acids and conversion of the acids to a mixed anhydride and reaction of the latter with ammonia or an appropriate amine to form the amides.

21 Claims, No Drawings

β-(HEXAHYDRO-2,6-METHANO-3-BENZAZOCIN-11-YL)PROPIONIC ACIDS, ESTERS AND AMIDES

RELATED APPLICATIONS

This is a continuation-in-part of our prior, copending application Ser. No. 886,650, filed Mar. 15, 1978, abandoned May 4, 1979.

BACKGROUND OF THE INVENTION (a) Field of the Invention

This invention relates to β-(hexahydro-2,6-methano-3-benzazocin-11-yl)propionic acids, esters and amides, useful as analgesics and narcotic antagonists.

(b) Description of the Prior Art

Michne, U.S. Pat. No. 3,932,422, patented Jan. 13, 1976, describes certain 1,2,3,4,5,6-hexahydro-2,6-methano-3-benzazocines having an 11(eq)-alkyl side chain bearing ketone or carbinol functions, and other art, for example Archer, U.S. Pat. No. 3,250,678, patented May 10, 1966, describes 1,2,3,4,5,6-hexahydro-2,6-methano-3-benzazocines having unsubstituted lower-alkyl groups at the 11-position, for example methyl or ethyl. However, such 1,2,3,4,5,6-hexahydro-2,6-methano-3-benzazocines having an 11-alkyl side chain substituted with other functional groups, such as a carboxylic acid group or esters or amides thereof, are unknown in the art.

SUMMARY OF THE INVENTION

In a composition of matter aspect, the present invention relates to certain β-[3-$R_1$-6(eq)-$R_4$-7-$R_2''$-8-$R_2$-9-$R_2'$-10-$R_2'''$-11(ax)-$R_3$-1,2,3,4,5,6-hexahydro-2,6-methano-3-benzazocin-11(eq)-yl]propionic acids, and lower-alkyl esters and unsubstituted, N-lower-alkyl, N,N-di-lower-alkyl and N-(carbo-lower-alkoxy-lower-alkyl)amides thereof, which are useful as analgesics and narcotic antagonists.

DETAILED DESCRIPTION INCLUSIVE OF THE PREFERRED EMBODIMENTS

More specifically, this invention provides compounds having the formula:

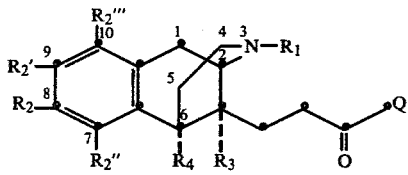

and chemically designated 3-$R_1$-6(eq)-$R_4$-7-$R_2''$-8-$R_2$-9-$R_2'$-10-$R_2'''$-11(ax)-$R_3$-11(eq)-($CH_2CH_2CO$-Q)-1,2,3,4,5,6-hexahydro-2,6-methano-3-benzazocines, which are useful as analgesics and narcotic antagonists, and wherein $R_1$ is hydrogen, lower-alkyl, cycloalkyl-lower-alkyl, phenyl-lower-alkyl, lower-alkenyl or lower-alkynyl; $R_2$, $R_2'$, $R_2''$ and $R_2'''$ are each hydrogen, or three of them are hydrogen and the fourth is hydroxy, lower-alkoxy, methoxymethoxy ($CH_3OCH_2O$) or benzyloxy; $R_3$ and $R_4$ are each hydrogen or lower-alkyl, or $R_3$ and $R_4$ together are divalent lower-alkylene, ($CH_2)_n$—, where n is one of the integers 3 or 4; and Q is hydroxy, lower-alkoxy, amino ($NH_2$), N-lower-alkylamino, N,N-di-lower-alkylamino or N-(carbo-lower-alkoxy-lower-alkyl)amino.

As used herein, the terms lower-alkyl or lower-alkoxy mean saturated, acyclic groups which may be straight or branched containing from one to about seven carbon atoms as exemplified by methyl, ethyl, propyl, isopropyl, butyl, methoxy, ethoxy, propoxy, isopropoxy or butoxy.

As used herein, the terms lower-alkenyl and lower-alkynyl mean monovalent groups of from three to seven carbon atoms containing one double or triple bond as illustrated, for example, by 1-propenyl, 2-butenyl, 4-pentenyl, 3-methyl-2-butenyl, 1-methyl-2-propenyl, 2-methyl-2-propenyl, 2-propynyl, 2-butynyl, 4-pentynyl, 2-hexynyl and the like.

As used herein, the term cycloalkyl means saturated carbocyclic groups containing from three to seven ring carbon atoms as illustrated, for example, by cyclopropyl, cyclobutyl, cyclopentyl, cyclohexyl, 2-methylcyclobutyl, 4-ethylcyclohexyl and the like.

The compounds of Formula I where Q is lower-alkoxy are prepared by heating a di-lower-alkyl 1-$R_1$-4aα-$R_3$-5α-$R_4$-6-$R_2''$-7-$R_2$-8-$R_2'$-9-$R_2'''$-1,2,3,4,4a,5,10,10a-octahydro-2,5-methanobenzo[g]quinoline-3,3-dicarboxylate having the formula

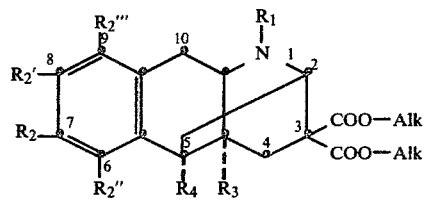

where $R_1$, $R_2$, $R_2'$, $R_2''$, $R_2'''$, $R_3$ and $R_4$ have the meanings given above, and Alk is lower-alkyl, with formic acid in an inert organic solvent at a temperature from 100°–150° C. or with a benzyl-di-lower-alkylammonium formate or a tri-lower-alkylammonium formate at a temperature in the range from 120°–150° C. The reaction results in ring opening between the 2- and 3- ring carbon atoms of the compounds of Formula II followed by decarbalkoxylation of the 3-carbo-lower-alkoxy group, COO-Alk. Suitable solvents are toluene, xylene or mesitylene. A preferred reaction medium is formic acid in mesitylene. A particularly preferred method involves ring opening in trimethylammonium formate.

The compounds of Formula I where Q is hydroxy, i.e. the carboxylic acids, are prepared from the corresponding esters (Q is lower-alkoxy) by hydrolyzing the latter either with aqueous alkali, for example, aqueous sodium hydroxide or potassium hydroxide, or with an aqueous mineral acid, for example, aqueous hydrobromic or hydrochloric acids. When hydrolysis is effected in aqueous alkali the reaction is advantageously carried out by heating a solution of the ester and a molar excess of alkali in a lower-alkanol or a lower-alkanol/water solution, neutralizing the reaction medium and isolating the product from the neutral solution. When hydrolysis is effected with aqueous mineral acid, the reaction is advantageously carried out by refluxing a solution of the ester in the aqueous acid, neutralizing the reaction medium and isolating the product from the neutral solution. In the case when aqueous hydrobromic acid is used for the hydrolysis, the reaction also results in cleavage of any ether groups in the molecule, for example, when $R_2$, $R_2'$, $R_2''$ or $R_2'''$ is lower-alkoxy, methoxymethoxy or benzyloxy, and the product isolated is thus the compound where the corresponding group is hydroxy.

The compounds of Formula I where Q is amino, N-lower-alkylamino, N,N-di-lower-alkylamino or N-(carbo-lower-alkoxy-lower-alkyl)amino are prepared by reacting the corresponding carboxylic acids (Q is hydroxy) with dicyclohexylcarbodiimide and reacting the resulting mixed anhydride with ammonia or with an appropriate N-lower-alkyl-, N,N-di-lower-alkyl- or N-(carbo-lower-alkoxy-lower-alkyl)amine in an inert organic solvent, for example, acetonitrile, toluene or tetrahydrofuran. The reaction is carried out at a temperature from 0° to about 40° C., and a preferred solvent is acetonitrile.

The compounds of Formula I where one of $R_2$, $R_2'$, $R_2''$ and $R_2'''$ is methoxymethoxy are prepared by reaction of the corresponding compounds where the corresponding group is hydroxy with dimethoxymethane in the presence of a catalytic amount of a strong acid and in an inert organic solvent. The reaction is carried out by refluxing a solution of the reactants in the chosen solvent, for example chloroform, methylene dichloride, ethylene dichloride and the like, under a Soxhlet extractor containing molecular sieves having a pore size sufficient to trap and hold molecules of methanol. In this way the methanol produced in the reversible reaction is removed from the reaction mixture as it is formed, and the reaction proceeds to completion. It has been found that 4 A molecular sieves have a porosity of the proper size for this purpose.

The compounds of Formula I where one of $R_2$, $R_2'$, $R_2''$ and $R_2'''$ is methoxymethoxy are particularly useful as intermediates for preparing the corresponding compounds where the corresponding group is hydroxy and which contain acid sensitive groups elsewhere in the molecule, for example compounds where $R_1$ is cycloalkyl-lower-alkyl where cycloalkyl is cyclopropyl, since the methoxymethoxy group is readily cleaved under mild acid conditions. In fact an alternative method for preparing the compounds of Formula I where one of $R_2$, $R_2'$, $R_2''$ and $R_2'''$ is hydroxy and Q is lower-alkoxy comprises heating a compound of Formula II where one of $R_2$, $R_2'$, $R_2''$ and $R_2'''$ is methoxymethoxy with formic acid in an inert organic solvent or with a benzyl-di-lower-alkylammonium formate or a tri-lower-alkylammonium formate as described above. The conditions of the reaction are sufficiently acidic to effect not only ring opening of the compounds of Formula II to produce the compounds of Formula I but also to effect cleavage of the methoxymethoxy group to the hydroxy group.

The compounds of Formula II where one of $R_2$, $R_2'$, $R_2''$ and $R_2'''$ is methoxymethoxy are prepared from the corresponding compounds where the corresponding group is hydroxy in the same manner as described above with respect to the preparation of the compounds of Formula I where one of the subject groups is methoxymethoxy.

The compounds of Formula I where $R_1$ is benzyl or where one of $R_2$, $R_2'$, $R_2''$ and $R_2'''$ is benzyloxy can be catalytically debenzylated to give the corresponding compounds where $R_1$ is hydrogen or one of $R_2$, $R_2'$, $R_2''$ and $R_2'''$ is hydroxy, as the case may be. The resulting compounds where $R_1$ is hydrogen can then be realkylated, as described below, with an appropriate alkylating agent to give other different compounds where $R_1$ has the meanings, other than hydrogen, given above. Reduction is carried out in an inert organic solvent, for example ethanol, isopropanol, and the like, and at pressures from 40 to 100 p.s.i.g. A preferred catalyst is palladium-on-charcoal. The alkylation of the compounds of Formula I where $R_1$ is hydrogen is carried out in an inert organic solvent, for example acetone, ethanol or dimethylformamide (hereinafter DMF), and in the presence of an acid-acceptor, for example alkali metal carbonates or bicarbonates.

The compounds of Formula I where $R_1$ is benzyl or where one of $R_2$, $R_2'$, $R_2''$ and $R_2'''$ is benzyloxy are thus useful as intermediates for preparing other compounds of Formula I where these variables have the other meanings indicated above.

The compounds of Formula I where $R_1$ is lower-alkenyl, lower-alkynyl, cycloalkyl-lower-alkyl or phenyl-lower-alkyl (e.g. phenylethyl) are advantageously prepared from the corresponding compounds where $R_1$ is hydrogen by reaction of the latter with an appropriate lower-alkenyl halide, lower-alkynyl halide, cycloalkyl-lower-alkyl halide or phenyl-lower-alkyl halide, as the case may be, in an inert organic solvent, for example a lower-alkanol, acetone or DMF, in the presence of an acid-acceptor, for example an alkali metal carbonate or bicarbonate. A preferred solvent is DMF.

The compounds of Formula II and the method of their preparation are disclosed in our U.S. patent application Ser. No. 818,713, filed July 25, 1977, now U.S. Pat. No. 4,119,628, patented Oct. 10, 1978, and continuation-in-part application thereof Ser. No. 878,308, filed Feb. 16, 1978, now U.S. Pat. No. 4,148,794, patented Apr. 10, 1979, the disclosures of which are incorporated herein by reference.

Due to the presence of a basic amino grouping, the free base forms represented by Formula I above react with organic and inorganic acids to form acid-addition salts. The acid-addition salt forms are prepared from any organic or inorganic acid. They are obtained in conventional fashion, for instance either by direct mixing of the base with the acid or, when this is not appropriate, by dissolving either or both of the base and the acid separately in water or an organic solvent and mixing the two solutions, or by dissolving both the base and the acid together in a solvent. The resulting acid-addition salt is isolated by filtration, if it is insoluble in the reaction medium, or by evaporation of the reaction medium to leave the acid-addition salt as a residue. The acid moieties or anions in these salt forms are in themselves neither novel nor critical and therefore can be any acid anion or acid-like substance capable of salt formation with the base.

Representative acids for the formation of the acid-addition salts include formic acid, acetic acid, isobutyric acid, alpha-mercaptopropionic acid, trifluoroacetic acid, malic acid, fumaric acid, succinic acid, succinamic acid, tannic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicylic acid, 3,5-dinitrobenzoic acid, anthranilic acid, cholic acid, 2-pyridinecarboxylic acid, pamoic acid, 3-hydroxy-2-napthoic acid, picric acid, quinic acid, tropic acid, 3-indoleacetic acid, barbituric acid, sulfamic acid, methanesulfonic acid, ethanesulfonic acid, isethionic acid, benzenesulfonic acid, p-toluenesulfonic acid, butylarsonic acid, methanephosphonic acid, acidic resins, hydrofluoric acid, hydrochloric acid, hydrobromic acid, hydroiodic acid, perchloric acid, nitric acid, sulfuric acid, phosphoric acid, arsenic acid and the like.

All of the acid-addition salts are useful as sources of the free base forms, by reaction with an inorganic base. It will thus be appreciated that if one or more of the characteristics, such as solubility, molecular weight, physical appearance, toxicity or the like of a given base or acid-addition salt thereof render that form unsuitable for the purpose at hand, it can be readily converted to another, more suitable form. For pharmaceutical purposes, acid-addition salts of relatively non-toxic, pharmaceutically-acceptable acids, for example hydrochloric acid, lactic acid, tartaric acid, and the like, are of course employed.

The compounds of this invention can exist in enantiomeric forms separable into enantiomers. If desired, the isolation or the production of a particular enantiomeric form can be accomplished by application of general principles known in the prior art. In the nomenclature employed for the compounds of Formula I herein, "ax" stands for axial and "eq" for equatorial, and the configurations are given with reference to the hydroaromatic ring. Thus, the 6(eq), 11(ax) compounds of Formula I are in the cis configuration, whereas the 6(eq), 11(eq) compounds are in the trans configuration.

In the nomenclature employed for the compounds of Formula II, again configurations are given with reference to the hydroaromatic ring, and the designation "$\beta$" indicates the cis configuration relative to the 2,5-methano bridge of the compounds of Formula II. Conversely, the designation "$\alpha$" indicates the trans configuration relative to the same groups.

In standard pharmacological test procedures, the compounds of Formula I and the acid-addition salts thereof have been found useful as depressants of the central nervous system, and more particularly have been found useful as analgesics and as antagonists of strong analgesics such as phenazocine, meperidine and morphine.

The compounds of Formula I can be administered in the same manner as known analgesics and antagonists of strong analgesics, i.e. parenterally or orally in any of the conventional pharmaceutical forms, as for instance solutions, suspensions, tablets, capsules and the like.

As described above and as will be seen hereinbelow, many of the species of Formula I are readily interconvertible by simple and well-known reactions such as hydrolysis, esterification, etherification, and the like, so that they are also useful as intermediates for each other.

The useful properties of the compounds of this invention were demonstrated by standard pharmacological procedures readily carried out by technicans having ordinary skill in pharmacological test procedures, so that the actual determination of numerical biological data definitive for a particular test compound can be ascertained without the need for any extensive experimentation.

The test procedures used to determine the analgesic and narcotic antagonist activities of the compounds of the invention have been described in detail in the prior art and are as follows: the acetylcholine-induced abdominal constriction test, which is a primary analgesic screening test designed to measure the ability of a test agent to suppress acetylcholine-induced abdominal constriction in mice, described by Collier et al., Brit. J. Pharmacol. Chemotherap. 32, 295 (1968); a modification of the anti-bradykinin test, which is also a primary analgesic screening procedure, described by Berkowitz et al., J. Pharmacol. Exp. Therap. 177, 500–508 (1971), Blane et al., J. Pharm. Pharmacol. 19, 367–373 (1967), Botha et al., Eur. J. Pharmacol. 6, 312–321 (1969) and Deffenu et al., J. Pharm. Pharmacol. 18, 135 (1966); the phenyl-p-quinone-induced writhing test, also a primary analgesic screening test, designed to measure the ability of a test agent to prevent phenyl-p-quinone-induced writhing in mice, described by Pearl and Harris, J. Pharmacol. Exptl. Therap. 154, 319–323 (1966); the rat tail flick radiant thermal heat analgesic (agonist) test described by D'Amour and Smith, J. Pharmacol. Exptl. Therap. 72, 74 (1941) as modified by Bass and Vander-Brook, J. Am. Pharm. Assoc. Sci. Ed. 41, 569 (1956); the phenazocine antagonist test, which is designed to measure the ability of a test agent to antagonize the effect of phenazocine in the above-identified rat tail flick response test, described by Harris and Pierson, J. Pharmacol. Exptl. Therap. 143, 141 (1964); and the Straub tail test which is an observation of erection and arching of the tail in mice and which is characteristic of narcotic analgesics, such as morphine, first described by Straub, Dtsch. med. Wochr. (1911), page 1426 and further described by Aceto et al., Brit. J. Pharmacol. 36, 225–239 (1969).

The structures of the compounds of this invention were established by the modes of synthesis, by elementary analyses and by ultraviolet, infrared and nuclear magnetic resonance spectra. The course of reactions and homogeneity of the products were ascertained by thin layer chromatography.

The manner and process of making and using the invention, and the best mode contemplated by the inventors of carrying out this invention will now be described so as to enable any person skilled in the art to which it pertains to make and use the same. The melting points are uncorrected.

EXAMPLE 1

A. A solution of 30 ml. of trimethylammonium formate [prepared by dissolving 189 ml. (1.0 mole) of trimethylamine in 94 ml. (2.5 moles) of formic acid] was heated to 100° C. on a hot plate, 8.3 g. (0.02 mole) of diethyl 1,4a$\alpha$,5$\alpha$-trimethyl-7-methoxy-1,2,3,4,4a,5,10,-10a-octahydro-2,5-methanobenzo[g]quinoline-3,3-dicarboxylate was added, and the mixture was heated under reflux at 145°–150° C. for thirteen minutes. The mixture was then poured onto ice, basified with excess 3 N sodium hydroxide and extracted with diethyl ether. The ether extracts were washed with brine, dried over magnesium sulfate and taken to dryness to give 6.5 g. of a colorless oil which was crystallized from hexane to give 3.8 g. of ethyl $\beta$-[3,6(eq),11(ax)-trimethyl-8-methoxy-1,2,3,4,5,6-hexahydro-2,6-methano-3-benzazocin-11(eq)-yl]propionate, m.p. 91°–93° C.

The base was resolved into its optical isomers by reaction in 95% ethanol with (−)-dibenzoyltartaric acid monohydrate ($[\alpha]_D^{25} = -109.4°$, m.p. 93°–95° C.) to give (−)-ethyl $\beta$-[3,6(eq),11(ax)-trimethyl-8-methoxy-1,2,3,4,5,6-hexahydro-2,6-methano-3-benzazocin-11(eq)-yl]propionate dibenzoyltartrate which, after several recrystallizations from 95% ethanol, afforded material having m.p. 160°–161° C., $[\alpha]_D^{25} = -81.2°$.

The filtrate from the treatment with (−)-dibenzoyltartaric acid monohydrate was taken to dryness, the residue treated with excess 10% sodium hydroxide and the mixture extracted with diethyl ether. The free base obtained by evaporation to dryness of the extracts was dissolved in 95% ethanol and the solution treated with a molar equivalent amount of (+)-dibenzoyltartaric acid monohydrate ($[\alpha]_D^{25} = +111.8°$) to give (+)-ethyl β-[3,6(eq),11(ax)-trimethyl-8-methoxy-1,2,3,4,5,6-hexahydro-2,6-methano-3-benzazocin-11(eq)-yl]propionate dibenzoyltartrate which, after several recrystallizations from 95% ethanol, afforded material having m.p. 160°–161° C., $[\alpha]_D^{25} = -83.0°$.

Cleavage of the (−) and the (+) dibenzoyltartrates afforded the respective levo (m.p. 50°–52° C., $[\alpha]_D^{25} = -77.8°$) and dextro (m.p. 51°–52° C., $[\alpha]_D^{25} = +79.7°$) free bases.

B. Following a procedure similar to that described in Example 1A above, a solution of 11.7 g. (0.024 mole) of diethyl 1-benzyl-4aα,5α-dimethyl-7-methoxy-1,2,3,4,4a,5,10,10a-octahydro-2,5-methanobenzo[g]quinoline-3,3-dicarboxylate in 60 ml. of trimethylammonium formate was heated at 160°–170° C. for one hour and fifteen minutes. Workup of the reaction mixture in the manner described in part A above and isolation of the product in the form of the hydrochloride salt afforded 2.9 g. of ethyl β-[3-benzyl-6(eq),11(ax)-dimethyl-8-methoxy-1,2,3,4,5,6-hexahydro-2,6-methano-3-benzazocin-11(eq)-yl]propionate hydrochloride, m.p. 201°–203° C.

EXAMPLE 2

A. A solution of 6.2 g. (0.018 mole) of the (+)-ethyl β-[3,6(eq),11(ax)-trimethyl-8-methoxy-1,2,3,4,5,6-hexahydro-2,6-methano-3-benzazocin-11(eq)-yl]propionate described above in Example 1 in 100 ml. of 48% hydrobromic acid was heated under reflux under a nitrogen atmosphere for about three hours, concentrated to dryness, and the residual solid recrystallized from distilled water to give 6.4 g. of β-[3,6(eq),11(ax)-trimethyl-8-hydroxy-1,2,3,4,5,6-hexadhydro-2,6-methano-3-benzazocin-11(eq)-yl]propionic acid, m.p. 301°–303° C.

The latter, along with 0.1 g. of p-toluenesulfonic acid monohydrate, was dissolved in 150 ml. of ethylene dichloride and 50 ml. of methanol, and the mixture was refluxed for seveal hours, then washed with saturated sodium bicarbonate. The organic solution was dried and taken to dryness and the residue treated with an ethereal solution of hydrochloric acid. The solid which separated was collected, dried and recrystallized from methanol to give 4.7 g. of (+)-methyl β-[3,6(eq),11(ax)-trimethyl-8-hydroxy-1,2,3,4,5,6-hexahydro-2,6-methano-3-benzazocin-11(eq)-yl]propionate hydrochloride, m.p. 260°–263° C., $[\alpha]_D^{25} = +28.7°$.

B. Similarly, 2.2 g. (0.0064 mole) of (−)-ethyl β-[3,6(eq),11(ax)-trimethyl-8-methoxy-1,2,3,4,5,6-hexahydro-2,6-methano-3-benzazocin-11(eq)-yl]propionate was cleaved with 45 ml. of 48% hydrobromic acid under nitrogen to give 2.0 g. of (−)-β-[3,6(eq),11(ax)-trimethyl-8-hydroxy-1,2,3,4,5,6-hexahydro-2,6-methano-3-benzazocin-11(eq)-yl]propionic acid, m.p. 297°–300° C.

The latter was esterified in a solution of 50 ml. of methanol and 100 ml. of ethylene dichloride containing 0.1 g. of p-toluenesulfonic acid. The product was isolated in the form of the hydrochloride salt which was recrystallized from methanol/diethyl ether to give 1.4 g. of (−)-methyl β-[3,6(eq),11(ax)-trimethyl-8-hydroxy-1,2,3,4,5,6-hexahydro-2,6-methano-3-benzazocin-11(eq)-yl]propionate hydrochloride, m.p. 259°–262° C., $[\alpha]_D^{25} = -26.5°$ C.

EXAMPLE 3

Following a procedure similar to that described in Example 2 above, 10.5 g. (0.03 mole) of ethyl β-[3,6(eq),11(ax)-trimethyl-8-methoxy-1,2,3,4,5,6-hexahydro-2,6-methano-3-benzazocin-11(eq)-yl]propionate was cleaved with 75 ml. of 48% hydrobromic acid under nitrogen to give crude β-[3,6(eq),11(ax)-trimethyl-8-hydroxy-1,2,3,4,5,6-hexahydro-2,6-methano-3-benzazocin-11(eq)-yl]propionic acid which, without further purification, was reesterified with ethanol in the presence of hydrogen chloride to give 6.2 g. of ethyl β-[3,6(eq),11(ax)-trimethyl-8-hydroxy-1,2,3,4,5,6-hexahydro-2,6-methano-3-benzazocin-11(eq)-yl]propionate hydrochloride, m.p. 258°–261° C. (from ethanol/diethyl ether).

EXAMPLE 4

Following a procedure similar to that described in Example 2 above, 29.7 g. (0.086 mole) of ethyl β-[3,6(eq),11(ax)-trimethyl-8-methoxy-1,2,3,4,5,6-hexahydro-2,6-methano-3-benzazocin-11(eq)-yl]propionate was cleaved with 48% hydrobromic acid to give 13.2 g. of β-[3,6(eq),11(ax)-trimethyl-8-hydroxy-1,2,3,4,5,6-hexahydro-2,6-methano-3-benzazocin-11(eq)-yl]propionic acid hydrobromide, m.p. 297°–300° C. (from ethanol).

The latter (2.5 g., 0.006 mole) was converted to the corresponding butyl ester by reaction with 75 ml. of n-butanol in the presence of 0.1 g. of p-toluenesulfonic acid. The product was isolated in the form of the hydrochloride salt to give 1.5 g. of butyl β-[3,6(eq),11(ax)-trimethyl-8-hydroxy-1,2,3,4,5,6-hexahydro-2,6-methano-3-benzazocin-11(eq)-yl]propionate hydrochloride, m.p. 263°–266° C. (from acetone/diethyl ether).

EXAMPLE 5

A solution of 5 g. (0.013 mole) of ethyl β-[3,6(eq),1-1(ax)-trimethyl-8-methoxy-1,2,3,4,5,6-hexahydro-2,6-methano-3-benzazocin-11(eq)-yl]propionate hydrochloride in 25 ml. of water and 5 ml. of concentrated hydrochloric acid was heated under reflux for about twelve hours, and cooled. The solid which separated was collected and dried to give 4.4 g. of β-[3,6(eq),11(ax)-trimethyl-8-methoxy-1,2,3,4,5,6-hexahydro-2,6-methano-3-benzazocin-11(eq)-yl]propionic acid hydrochloride, m.p. 244°–247° C.

EXAMPLE 6

The ethyl β-[3,6(eq),11(ax)-trimethyl-8-hydroxy-1,2,3,4,5,6-hexahydro-2,6-methano-3-benzazocin-11(eq)-yl]propionate hydrochloride described above in Example 3 (11.0 g., 0.03 mole) was converted to the base, and the latter dissolved in 150 ml. of dimethylformamide (DMF) was treated first with 1.9 g. (0.045 mole) of a 55% mineral oil dispersion of sodium hydride, stirred for about an hour and a half and then treated with a solution of 5.6 g. (0.044 mole) of benzyl chloride in 10 ml. of DMF and stirred for three hours at ambient temperature. The mixture was poured into 500 ml. of ice/water, extracted two times with diethyl ether, the ether extracts washed twice with brine, then dried and taken to dryness. There was thus obtained 15 g. of an oil which solidified on standing and which was recrystallized twice from hexane to give 8.0 g. of ethyl β-[3,6(eq),11(ax)-trimethyl-8-benzyloxy-1,2,3,4,5,6-hexahydro-2,6-methano-3-benzazocin-11(eq)-yl]propionate, m.p. 105°–107° C.

The latter was dissolved in a solution of 50 ml. of water and 150 ml. of isopropanol containing 1.5 g. of sodium hydroxide, and the mixture was heated under reflux for about twelve hours, neutralized to about pH 7, concentrated to dryness, and the residue converted to the hydrochloride salt which was recrystallized from water to give 1.37 g. of β-[3,6(eq),11(ax)-trimethyl-8-benzyloxy-1,2,3,4,5,6-hexahydro-2,6-methano-3-benzaocin-11(eq)-yl]propionic acid hydrochloride, m.p. 244°-246° C.

EXAMPLE 7

A solution of 5.0 g. (0.012 mole) of β-[3,6(eq),11(ax)-trimethyl-8-benzyloxy-1,2,3,4,5,6-hexahydro-2,6-methano-3-benzazocin-11(eq)-yl]propionic acid, 5.1 g. (0.023 mole) of dicyclohexylcarbodiimide and 1.0 g. (0.014 mole) of n-butylamine in 125 ml. of acetonitrile was stirred at ambient temperature for twenty-one hours. The reaction mixture was then filtered and the filtrate taken to dryness in vacuo to give a gum which was triturated with water, dilute sodium hydroxide and ether. The resulting solid was collected and dried to give 3.5 g. of crude product which was recrystallized from methanol to give 3.0 g. of β-[3,6(eq),11(ax)-trimethyl-8-benzyloxy-1,2,3,4,5,6-hexahydro-2,6-methano-3-benzazocin-11(eq)-yl]-N-butylpropionamide, m.p. 141°-143° C.

The latter (2.9 g., 0.006 mole) was dissolved in 100 ml. of absolute ethanol and reduced with hydrogen over 100 mg. of 10% palladium-on-charcoal under an initial hydrogen pressure of about 51 p.s.i.g. When reduction was complete in about four hours, the catalyst was removed by filtration, the filtrate evaporated to dryness and the residue dissolved in acetone and treated slowly with a molar equivalent amount of ethereal hydrogen chloride. The solid which separated was collected and recrystallized from methanol/diethyl ether to give 1.4 g. of β-[3,6(eq),11(ax)-trimethyl-8-hydroxy-1,2,3,4,5,6-hexahydro-2,6-methano-3-benzazocin-11-(eq)-yl]-N-butylpropionamide hydrochloride, m.p. 270°-275° C.

EXAMPLE 8

Following a procedure similar to that described in Example 7 above, a slurry of 3.3 g. (0.0077 mole) of β-[3,6(eq),11(ax)-trimethyl-8-benzyloxy-1,2,3,4,5,6-hexahydro-2,6-methano-3-benzazocin-11(eq)-yl]propionic acid hydrochloride in 100 ml. of acetonitrile was shaken with 3.2 g. (0.015 mole) of dicyclohexylcarbodiimide and the mixture treated with another slurry of 1.0 g. (0.007 mole) of methyl glycinate hydrochloride and 0.8 g. (0.008 mole) of triethylamine in 25 ml. of acetonitrile. The combined mixture was stirred at ambient temperature for about twenty-eight hours. The product was converted to the hydrochloride salt to give 2.5 g. of β[3,6(eq),11(ax)-trimethyl-8-benzyloxy-1,2,3,4,5,6-hexahydro-2,6-methano-3-benzazocin-11(eq)-yl]-N-(carbomethoxymethyl)propionamide hydrochloride, m.p. 130°-133° C.

The latter was catalytically debenzylated in methanol over 100 mg. of 10% palladium-on-charcoal using the procedure described above in Example 7, and the product converted to the hydrochloride salt which was recrystallized from acetone to give β-[3,6(eq),11(ax)-trimethyl-8-hydroxy-1,2,3,4,5,6-hexahydro-2,6-methano-3-benzazocin-11(eq)-yl]-N-(carbomethoxymethyl)propionamide hydrochloride, m.p. 148°-150° C.

EXAMPLE 9

Following a procedure similar to that described in Example 7 above 3.5 g. (0.01 mole) of β-[3,6(eq),11(ax)-trimethyl-8-methoxy-1,2,3,4,5,6-hexahydro-2,6-methano-3-benzazocin-11(eq)-yl]propionic acid was reacted with 2.1 g. (0.01 mole) of dicyclohexylcarbodiimide and 2.16 ml. (0.021 mole) of diethylamine in 25 ml. of acetonitrile and the product recrystallized from hexane to give 2.0 g. of β-[3,6(eq),11(ax)-trimethyl-8-methoxy-1,2,3,4,5,6-hexahydro-2,6-methano-3-benzazocin-11(eq)-yl]-N,N-diethylpropionamide, m.p. 87°-89° C.

EXAMPLE 10

To a solution of 6.7 g. (0.018 mole) of β-[3,6(eq),1-1(ax)-trimethyl-8-methoxy-1,2,3,4,5,6-hexahydro-2,6-methano-3-benzazocin-11(eq)-yl]-N,N-dimethylpropionamide in 90 ml. of DMF was added 4.3 g. (0.09 mole) of a 50% mineral oil dispersion of sodium hydride. The mixture was then treated dropwise with stirring with 8.3 ml. (0.09 mole) of propanethiol. The mixture was refluxed for two hours, cooled, treated with an additional 4.3 g. of a 50% sodium hydride in mineral oil dispersion and an additional 8.3 ml. of propanethiol, refluxed for an additional three hours, then cooled and poured into a solution containing 6 molar equivalents of methanesulfonic acid. The solution was extracted with diethyl ether, the aqueous layer adjusted to pH 7.6 with alkali, and the crystals which separated were collected and dried to give 3.6 g. of crude product which was recrystallized from 95% ethanol to give 3.6 g. of β-[3,6(eq),11(ax) -trimethyl-8-hydroxy-1,2,3,4,5,6-hexahydro-2,6-methano-3-benzazocin-11(eq)-yl]-N,N-diethylpropionamide, m.p. 233°-235° C.

EXAMPLE 11

Following a procedure similar to that described in Example 7 above, 11.3 g. (0.032 mole) of β-[3,6(eq),1-1(ax)-trimethyl-8-methoxy-1,2,3,4,5,6-hexahydro-2,6-methano-3-benzazocin-11(eq)-yl]propionic acid hydrochloride was dissolved in a solution of 80 ml. of acetonitrile and 8.0 ml. (0.067 mole) of N-butyl-N-methylamine and the solution treated with 7.0 g. (0.034 mole) of dicyclohexylcarbodiimide to give 11.2 g. of β-[3,6(eq),11(ax)-trimethyl-8-methoxy-1,2,3,4,5,6-hexahydro-2,6-methano-3-benzazocin-11(eq)-yl]-N-butyl-N-methylpropionamide as a straw-colored syrup.

The latter (6.0 g., 0.016 mole) was cleaved with 0.08 mole of sodium propylsulfide in 80 ml. of dry DMF using the procedure described above in Example 10. The product was recrystallized from acetonitrile/ethanol to give 3.6 g. of β-[3,6(eq),11(ax)-trimethyl-8-hydroxy-1,2,3,4,5,6-hexahydro-2,6-methano-3-benzazocin-11(eq)-yl]-N-butyl-N-methylpropionamide, m.p. 184°-187° C.

EXAMPLE 12

Following a procedure similar to that described in Example 2 above, 8.0 g. (0.023 mole) of ethyl 62-[3,6(eq),11(ax)-trimethyl-8-methoxy-1,2,3,4,5,6-hexahydro-2,6-methano-3-benzazocin-11(eq)-yl]propionate was cleaved with 80 ml. of 48% hydrobromic acid, and the product, β-[3,6-(eq),11(ax)-trimethyl-8-hydroxy-1,2,3,4,5,6-hexahydro-2,6-methano-3-benzazocin-11(eq)-yl]propionic acid, was isolated as the ethane-sulfonate salt (8.9 g., m.p. 225°-230° C./from methanol/diethyl ether).

The latter was reconverted to the free base and the latter (5 g.) was esterified in a solution of 100 ml. of methanol and 100 ml. of chloroform containing five drops of ethanesulfonic acid using the procedure described above in Example 2, and the product was isolated in the form of the ethanesulfonate salt to give 4.45 g. of methyl β-[3,6(eq),11(ax)-trimethyl-8-hydroxy-1,2,3,4,5,6-hexahydro-2,6-methano-3-benzazocin-11(eq)-yl]propionate ethanesulfonate, m.p. 268°–270° C.

The latter (4.3 g., 0.01 mole), in a solution containing 100 ml. of methylene dichloride, 50 ml. of dimethoxymethane and 0.5 ml. of ethanesulfonic acid, was heated under reflux under a Soxhlet extractor containing 4 A molecular sieves. After refluxing for about twenty hours, an additional 20 ml. of dimethoxymethane was added, and refluxing was continued for another twenty-four hours. The mixture was then poured into an ice/dilute sodium hydroxide mixture and the mixture extracted with methylene dichloride. The extracts, after workup in the usual manner, afforded an oil which was dissolved in diethyl ether and treated with a molar excess of ethanesulfonic acid in diethyl ether. The solid which separated was collected, dried and recrystallized from acetone/diethyl ether to give 2.0 g. of methyl β-[3,6(eq),11(ax)-trimethyl-8-methoxymethoxy-1,2,3,4,5,6-hexahydro-2,6-methano-3-benzazocin-11(eq)-yl]propionate ethanesulfonate, m.p. 157°–159° C.

EXAMPLE 13

Following procedures similar to those described in Examples 1, 6 and 7, it is contemplated that diethyl 1,5β-dimethyl-1,2,3,4,4a,5,10,10a-octahydro-2,5-methanobenzo[g]quinoline-3,3-dicarboxylate can be converted to ethyl β-[3,6(eq)-dimethyl-1,2,3,4,5,6-hexahydro-2,6-methano-3-benzazocin-11(eq)-yl]propionate by heating the former under reflux in trimethylammonium formate and the latter saponified to β-[3,6(eq)-dimethyl-1,2,3,4,5,6-hexahydro-2,6-methano-3-benzazocin-11(eq)-yl]propionic acid by heating with dilute aqueous acid and isolating the product from a neutral medium. Reaction of the latter with dicyclohexylcarbodiimide in DMF and reaction of the resulting mixed anhydride with isopropylamine affords β-[3,6(eq)-dimethyl-1,2,3,4,5,6-hexahydro-2,6-methano-3-benzazocin-11(eq)-yl]-N-isopropylpropionamide.

EXAMPLE 14

Following procedures similar to those described in Examples 1, 6 and 7, it is contemplated that diethyl 1,4aβ,5β-trimethyl-6-methoxy-1,2,3,4,4a,5,10,10a-octahydro-2,5-methanobenzo[g]quinoline-3,3-dicarboxylate, diethyl 1,4aβ,5β-trimethyl-8-methoxy-1,2,3,4,4a,5,10,10a-octahydro-2,5-methanobenzo[g]quinoline-3,3-dicarboxylate and diethyl 1,4aβ,5β-trimethyl-9-methoxy-1,2,3,4,4a,5,10,10a-octahydro-2,5-methanobenzo[g]quinoline-3,3-dicarboxylate can be converted, by heating under reflux in trimethylammonium formate, respectively, to ethyl β-[3,6(eq),11(ax)-trimethyl-7-methoxy-1,2,3,4,5,6-hexahydro-2,6-methano-3-benzazocin-11-(eq)-yl]propionate, ethyl β-[3,6(eq),11(ax)-trimethyl-9-methoxy-1,2,3,4,5,6-hexahydro-2,6-methano-3-benzazocin-11(eq)-yl]propionate and etnhyl β-[3,6(eq), 11(ax)-trimethyl-10-methoxy-1,2,3,4,5,6-hexahydro-2,6-methano-3-benzazocin-11(eq)-yl]propionate which can be saponified with dilute sodium hydroxide and the product isolated from a neutral medium to give, respectively, β-[3,6(eq),11(ax)-trimethyl-7-methoxy-1,2,3,4,5,6-hexahydro-2,6-methano-3-benzazocin-11(eq)-yl]propionic acid, β-[3,6(eq),11(ax)-trimethyl-9-methoxy-1,2,3,4,5,6-hexahydro-2,6-methano-3-benzazocin-11(eq)-yl]propionic acid and β-[3,6(eq),11(ax)-trimethyl-10-methoxy-1,2,3,4,5,6-hexahydro-2,6-methano-3-benzazocin-11(eq)-yl]propionic acid. Reaction of each of the latter with dicyclohexylcarbodiimide in DMF and reaction of the resulting respective mixed anhydrides with dimethylamine affords, respectively, β-[3,6(eq),11(ax)-trimethyl-7-methoxy-1,2,3,4,5,6-hexahydro-2,6-methano-3-benzazocin-11(eq)-yl]-N,N-dimethylpropionamide, β-[3,6(eq),11(ax)-trimethyl-9-methoxy-1,2,3,4,5,6-hexahydro-2,6-methano-3-benzazocin-11(eq)-yl]-N,N-dimethylpropionamide and β-[3,6(eq),11(ax)-trimethyl-10-methoxy-1,2,3,4,5,6-hexahydro-2,6-methano-3-benzazocin-11(eq)-yl]-N,N-dimethylpropionamide.

EXAMPLE 15

Following procedures similar to those described in Examples 1, 6 and 7, it is contemplated that diethyl 1-methyl-4aβ,5β-trimethylene-7-methoxy-1,2,3,4,4a,5,10,10a-octahydro-2,5-methanobenzo[q]quinoline-3,3-dicarboxylate and diethyl 1-methyl-4aβ,5β-tetramethylene-7-methoxy-1,2,3,4,4a,5,10,10a-octahydro-2,5-methanobenzo[g]quinoline-3,3-dicarboxylate can be converted, by heating under reflux in trimethylammonium formate, respectively, to ethyl β-[3-methyl-6(eq),11(ax)-trimethylene-8-methoxy-1,2,3,4,5,6-hexahydro-2,6-methano-3-benzazocin-11(eq)-yl]propionate and ethyl β-[3-methyl-6(eq),1-1(ax)-tetramethylene-8-methoxy-1,2,3,4,5,6-hexahydro-2,6-methano-3-benzazocin-11(eq)-yl]-propionate, which can be saponified with dilute sodium hydroxide and the product isolated from a neutral medium to give, respectively, β-[3-methyl-6(eq),11(ax)-trimethylene-8-methoxy-1,2,3,4,5,6-hexahydro-2,6-methano-3-benzazocin-11(eq)-yl]propionic acid and β-[3-methyl-6(eq),1-1(ax)-tetramethylene-8-methoxy-1,2,3,4,5,6-hexahydro-2,6-methano-3-benzazocin-11(eq)-yl]propionic acid. Reaction of each of the latter with dicyclohexylcarbodiimide in DMF and reaction of the resulting respective mixed anhydrides with ammonia affords, respectively, β-[3-methyl-6(eq),11(ax)-trimethylene-8-methoxy-1,2,3,4,5,6-hexahydro-2,6-methano-3-benzazocin-11(eq)-yl]propionamide and β-[3-methyl-6(eq),11(ax)-tetramethylene-8-methoxy-1,2,3,4,5,6-hexahydro-2,6-methano-3-benzazocin-11(eq)-yl]propionamide.

EXAMPLE 16

It is contemplated that catalytic debenzylation of the ethyl β-[3-benzyl-6(eq),11(ax)-dimethyl-8-methoxy-1,2,3,4,5,6-hexahydro-2,6-methano-3-benzazocin-11(eq)-yl]propionate described above in Example 1B with hydrogen over a palladium-on-charcoal catalyst using the procedure described above in Example 7, would afford ethyl β-[6(eq),11(ax)-dimethyl-8-methoxy-1,2,3,4,5,6-hexahydro-2,6-methano-3-benzazocin-11(eq)-yl]propionate which, on reaction with cyclopropylmethyl bromide, allyl bromide or propargyl bromide in DMF in the presence of a molar equivalent amount of sodium carbonate, would afford, respectively, ethyl β-[3-cyclopropylmethyl-6(eq),11(ax)-dimethyl-8-methoxy-1,2,3,4,5,6-hexahydro-2,6-methano-3-benzazocin-11(eq)-yl]propionate, β-[3-(3-propen-1-yl)-6(eq),11-(ax)-dimethyl-8-methoxy-1,2,3,4,5,6-hexahydro-2,6-methano-3-benzazocin-11(eq)-yl]propionate and ethyl β-[3-(3-propyn-1-yl)-6(eq),11(ax)-dimethyl-8-methoxy-1,2,3,4,5,6-hexahydro-2,6-methano-3-benzazocin-11(eq)-yl]propionate.

BIOLOGICAL TEST RESULTS

The compounds of Formula I are generally active in the acetylcholine-induced abdominal constriction test (Ach), a primary analgesic screening test, and also in the rat tail flick radiant thermal heat analgesic test (Tail Flick Agonist, T.F.Ag.) and also in the Straub tail test (Straub). A few species have also been tested and found active in the antibradykinin (BK) test which is also a primary analgesic screening procedure. Individual species have been found active in the phenazocine tail flick antagonist test (Phen) indicating activity of these latter species as analgesic antagonists. Data so obtained for the compounds, identified by reference to the preceding examples and expressed either in terms of the $ED_{50}$ (mg./kg., subcutaneous administration) or in terms of percent inhibition, are given below. All doses are expressed in milligrams per kilogram (mg./kg.). The letter "I" means inactive.

| Example | Ach | Phen | BK | T.F. Ag. | Straub |
|---------|-----|------|----|---------|--------|
| 1A(+) | 3.2 | I/80 | — | 21 | 10 |
| 1A(−) (a) | 0.96 | — | — | — | 5.0 |
| 1B | 79%/75 0%/25 | I/80 | — | I/120 | — |
| 2(−) (b) | 0.030 | I/0.1–1.0 | — | 1.45 | 0.75 |
| 2(±) (c) | 3.4 | I/80 | — | 57 | 25 |
| 3 | 0.057 | I/80 | — | 57 | 25 |
| 4 | 0.78 | I/80(i.p.) | 2.6 | 15%/60 52%/120 | 25,75 |
| 5 | 47%/75 27%/25 | I/80 | — | I/240 | — |
| 6 | 3.2 | I/80 | — | I/120 | 10 |
| 7 | 15 | 0.084 | 0%/10 | I/120 | — |
| 9 | 3.0 | I/80 | — | I/120 | — |
| 10 | 5.5 | I | I | I | — |
| 11 | 3.3 | 4.4 | 16 | I/240 | — |
| 12 | 2.7 | I/1.0, 10, 80 | — | 13.5 | — |

(a) (−)-(D)-dibenzoyltartrate
(b) (−)-methyl ester hydrochloride
(c) (+)-acid hydrobromide

We claim:

1. A compound having the formula

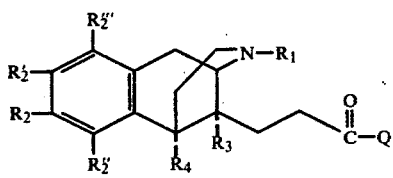

where $R_1$ is hydrogen, lower-alkyl, cycloloweralkyl-lower-alkyl, phenyl-lower-alkyl, lower-alkenyl or lower-alkynyl; $R_2$, $R_2'$, $R_2''$ and $R_2'''$ are each hydrogen, or three of them are hydrogen and the fourth is hydroxy, lower-alkoxy, methoxymethoxy or benzyloxy; $R_3$ and $R_4$ are each hydrogen or lower-alkyl, or $R_3$ and $R_4$ together are divalent lower-alkylene, $-(CH_2)_n-$, where n is one of the integers 3 or 4; and Q is hydroxy, lower-alkoxy, amino, N-lower-alkylamino, N,N-di-lower-alkylamino or N-(carbo-lower-alkoxy-lower-alkyl)amino; or an acid-addition salt thereof.

2. A compound according to claim 1 where one of $R_2$, $R_2'$, $R_2''$ and $R_2'''$ is hydroxy, lower-alkoxy, methoxymethoxy or benzyloxy.

3. A compound according to claim 2 where $R_2$ is hydroxy, lower-alkoxy, methoxymethoxy or benzyloxy.

4. A compound according to claim 3 where $R_3$ and $R_4$ are each lower-alkyl.

5. A compound according to claim 4 where Q is hydroxy.

6. A compound according to claim 4 where Q is lower-alkoxy.

7. A compound according to claim 4 where Q is amino, N-lower-alkylamino, N,N-di-lower-alkylamino or N-(carbo-lower-alkoxymethyl)amino.

8. A compound according to claim 7 where Q is n-lower-alkylamino or N,N-di-lower-alkylamino.

9. β-[3,6(eq),11(ax)-Trimethyl-8-hydroxy-1,2,3,4,5,6-hexahydro-2,6-methano-3-benzazocin-11(eq)-yl]propionic acid according to claim 5.

10. β-[3,6(eq),11(ax)-Trimethyl-8-methoxy-1,2,3,4,5,6-hexahydro-2,6-methano-3-benzazocin-11(eq)-yl]propionic acid according to claim 5.

11. β-[3,6(eq),11(ax)-Trimethyl-8-benzyloxy-1,2,3,4,5,6-hexahydro-2,6-methano-3-benzazocin-11(eq)-yl]propionic acid according to claim 5.

12. Ethyl β-[3,6(eq),11(ax)-trimethyl-8-methoxy-1,2,3,4,5,6-hexahydro-2,6-methano-3-benzazocin-11(eq)-yl]propionate according to claim 6.

13. Methyl β-[3,6(eq),11(ax)-trimethyl-8-hydroxy-1,2,3,4,5,6-hexahydro-2,6-methano-3-benzazocin-11(eq)-yl]propionate according to claim 6.

14. Ethyl β-[3,6(eq),11(ax)-trimethyl-8-hydroxy-1,2,3,4,5,6-hexahydro-2,6-methano-3-benzazocin-11(eq)-yl]propionate according to claim 6.

15. Butyl β-[3,6(eq),11(ax)-trimethyl-8-hydroxy-1,2,3,4,5,6-hexahydro-2,6-methano-3-benzazocin-11(eq)-yl]propionate according to claim 6.

16. Ethyl β-[3-benzyl-6(eq),11(ax)-dimethyl-8-methoxy-1,2,3,4,5,6-hexahydro-2,6-methano-3-benzozocin-11(eq)-yl]propionate according to claim 6.

17. Methyl β-[3,6(eq),11(ax)-trimethyl-8-methoxymethoxy-1,2,3,4,5,6-hexahydro-2,6-methano-3-benzazocin-11(eq)-yl]propionate according to claim 6.

18. β-[3,6(eq),11(ax)-Trimethyl-8-hydroxy-1,2,3,4,5,6-hexahydro-2,6-methano-3-benzazocin-11(eq)-yl]-N-butylpropionamide according to claim 8.

19. β-[3,6(eq),11(ax)-Trimethyl-8-methoxy-1,2,3,4,5,6-hexahydro-2,6-methano-3-benzazocin-11(eq)-yl]-N,N-diethylpropionamide according to claim 9.

20. β-[3,6(eq),11(ax)-Trimethyl-8-hydroxy-1,2,3,4,5,6-hexahydro-2,6-methano-3-benzazocin-11(eq)-yl]-N,N-diethylpropionamide according to claim 8.

21. β-[3,6(eq),11(ax)-Trimethyl-8-hydroxy-1,2,3,4,5,6-hexahydro-2,6-methano-3-benzazocin-11(eq)-yl]-N-butyl-N-methylpropionamide according to claim 8.

* * * * *

UNITED STATES PATENT AND TRADEMARK OFFICE
CERTIFICATE OF CORRECTION

PATENT NO. : 4,202,984
DATED : May 13, 1980
INVENTOR(S) : Thomas R. Lewis and William F. Michne It is certified that error appears in the above-identified patent and that said Letters Patent are hereby corrected as shown below:

Column 4, lines 60-61, change "napthoic" to read --naphthoic--.

Column 4, line 67, change "hydroiodic" to read --hydriodic--.

Column 13, lines 49-50, Claim 1, change "cyloloweralkyl-lower-alkyl" to read --cyclo-lower-alkyl-lower-alkyl--.

Column 14, line 17, Claim 8, change "n-lower-alkylamino" to read --N-lower-alkylamino--.

Column 14, lines 40-41, Claim 16, change "benzozocin" to read --benzazocin--.

Signed and Sealed this

Twenty-sixth Day of October 198.

[SEAL]

Attest:

GERALD J. MOSSINGHOFF

Attesting Officer     Commissioner of Patents and Trademarks